United States Patent [19]

Kohno et al.

[11] Patent Number: 5,631,221
[45] Date of Patent: May 20, 1997

[54] POLLENOSIS-INDUCING POLYPEPTIDE, PROCESS FOR PREPARING THE SAME, AND USES THEREOF

[75] Inventors: Keizo Kohno; Manami Sawatani; Masashi Kurimoto, all of Okayama, Japan

[73] Assignee: Kabushiki Kaisha Hayashibara Sibutsu Kagaku Kenkyujo, Okayama, Japan

[21] Appl. No.: 358,557

[22] Filed: Dec. 14, 1994

[30] Foreign Application Priority Data

Dec. 21, 1993 [JP] Japan ..................... 5-344700

[51] Int. Cl.$^6$ .................. A61K 38/16; A61K 39/00; C07K 1/00
[52] U.S. Cl. .................. 514/8; 514/2; 514/15; 514/17; 530/327; 530/330; 530/370; 530/379; 530/395; 530/406; 530/410; 530/411; 530/412; 530/413; 530/416; 530/418; 424/184.1; 424/185.1; 424/275.1; 424/276.1; 424/193.1
[58] Field of Search .................. 514/8, 2, 15, 17; 530/327, 330, 370, 379, 395, 406, 410, 411, 412, 413, 416, 417, 418; 424/185.1, 193.1, 275.1, 276.1, 184.1

[56] References Cited

U.S. PATENT DOCUMENTS

| | | | |
|---|---|---|---|
| 4,939,239 | 7/1990 | Matsuhashi et al. | 530/370 |
| 5,073,628 | 12/1991 | Matsuhashi et al. | 530/379 |

FOREIGN PATENT DOCUMENTS

| | | |
|---|---|---|
| 0308147 | 3/1989 | European Pat. Off. . |
| 0416816 | 3/1991 | European Pat. Off. . |
| 1156926 | 6/1989 | Japan . |
| 393730 | 4/1991 | Japan . |
| 9301213 | 1/1993 | WIPO . |

OTHER PUBLICATIONS

Koriyama et al, *Biochem. Biophys. Res. Commun.*, vol. 201, No.2, pp. 1021–1028, Jun. 15, 1994.
Namba et al, *FEBS Letters*, vol. 353, pp. 124–128, 1994.
Database WPI, Section Ch, Week 8832, Derwent Publication Ltd., London, GB; Class B04, AN 88–224232, JP63159324 (Lion Corp), 2 Jul. 1988.
Madoka Taniai et al. "N-terminal amino acid sequence of a major allergen of Japanese cedar pollen (Cry j I)", Elsevier Science Publishers B.V., vol. 239 No. 2, pp. 329–332 Nov. 1988.
Hiroshi Yasueda et al. "Isolation and partial characterization of the major allergen from Japanese cedar (Cryptomeria japonica) pollen", The Journal of Allergy and Clinical Immunology, vol. 71 No. 1, pp. 77–86, 1993.
Yasueda, H. et al., "Sugi Basic Protein", *Rinsho–Meneki (Clinical Immunology)*, vol. 20, No. 11, pp. 1047–1052 (1988).
Sawatani, M. et al., "Enzyme–Linked Immunosorbet Assay For The Quantification of Cry j I and Cry j II", *Allergy (Jap. J. of Allergology)*, vol. 43, No. 3, pp. 467–473 (1994).

Takahashi, Y. et al., "Protracted (Lasting) Presence Of Japanese Cedar Pollen Allergen (Cry j I) In House Dust", *Allergy (Jap. J. Allergology)*, vol. 43, No. 2, pp. 97–100 (1994).
Kawashima, T. et al. "Antigenic Analyses Of Sugi Basic Protein By Monoclonal Antibodies: I. Distribution and Characterization ob B–Cell–Tropic Epitopes of Cry j I Molecules", *Int. Arch. Allergy Immunol.*, vol. 98, pp. 110–117 (1992).
Kawashima, T. et al. "Antigenic Analyses of Sugi Baisc Protein By Monoclonal Antibodies: II. Detection Of Immunoreactive Gragments in Enzyme–Cleaved Cry j I'", *Int. Arch Allergy Immunol.*, vol. 98, pp. 118–126 (1992).
Taniai, M. et al., "Epitopes On Cry j I and Cry j II For Human IgE Antobodies Cross–Reactive Between Cupressus Sempervirens and Cryptomeria Japonica Pollen", *Molecular Immunolgy*, vol. 30, No. 2, pp. 183–189 (1993).
Taniguch, Y. et al., "Biological and Immunological Properties of Sugi Basic Protein–Pullulan Conjugate", *Int. Arch. Allergy Appl. Immunol.*, vol. 89, pp. 136–142 (1989).
Usui, M., et al., "Biological and Immunological Properties of Sugi Basic Protein–Pullulan Conjugate", *Int. Arch. Allergy Appl. Immunol.*, vol. 91, No. 1 pp. 74–79 (1990).
Usui, M., et al., "Biological and Immunological Properties of Antigen Pullulan Conjugate", *Trends in Glycotechnology*, vol. 4, No. 20, pp. 525–532 (Nov. 1992).
Sakaguchi et al., "Measurement Of Serum IgE Antibodies Against Japanese Cedar Pollen (Cryptomeri Japonica) in Japanese Monkeys (Macaca Fuscata) With Pollinosis", *J. Med Primatol*, vol. 21, pp. 323–327 (1992).
Sawatani, M. et al. "Immunological And Physicochemical Properties Of Cry j II, The Second Major Allergen Of Japanese Cedar Pollen (Cryptomeria Japonica)", *Jap. J. Allerg.*, vol. 42, No. 6 (1993).
Sakaguchi, M. et al., "Identification Of The Second Major Allergen Of Japanese Cedar Pollen", *Allgery*, vol. 45, pp. 309–312 (1990).
Taniai, M. et al., "N–Terminal Amino Acid Sequence Of A Major Allergen Of Japanese Cedar Pollen", *FEBS Ltrs.*, vol. 239, No. 2, pp. 329–332 (Nov. 1988).
Maiolini, R. et al., "Enxymoimmunoassay Of Human Alpha–Fetoprotein", *J. Immunol. Methods*, vol. 6, pp. 355–362 (1975).

(List continued on next page.)

*Primary Examiner*—Cecilia J. Tsang
*Assistant Examiner*—Abdel A. Mohamed
*Attorney, Agent, or Firm*—Browdy and Neimark

[57] ABSTRACT

A polypeptide having a molecular weight of 40,000±5,000 daltons and an isoelectric point of 9.5±0.5 is prepared from a cedar pollen. The polypeptide which induces pollenosis can be suitably used as desensitization agent because it induces immunoglobulin antibody which is effective for desensitization, but does not substantially induce immunoglobulin E antibody, a major factor causative of side effects including anaphylaxis shock. Therefore, the polypeptide can be advantageously used in the treatment, prevention and/or diagnosis of pollenosis.

17 Claims, No Drawings

OTHER PUBLICATIONS

Yoshitake, S. et al. "Mild And Efficient Conjugation of Rabbit Fab' And Horseradish Peroxidase Using A Maleimide Compounds And Its Use For Enzyme Immunoassay", *J. Biochem.*, Vo. 92, No. 5, (1982).

Mota, I. et al., "Homologous And Heterologous Passive Cutaneous Anaphylactic Activity Of MOuse Antisera During The Course Of Immunization", *Life Sciences,* vol. 8, Part II, pp. 813–820 (1969).

Yasueda, H. et al., "Isolation And Partial Characterization Of The Major Allergen From Japanese Cedar (Cryptomeria Japonica) Pollen", *J. Allergy Clin. Immunol.,* vol. 71, Part 1, pp. 77–86 (Jan. 1983).

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Arg Lys Val Glu His Ser Arg His Asp Ala Ile
1               5                   10

( 2 ) INFORMATION FOR SEQ ID NO:2:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Asn Leu Ser Pro Ser
1               5

POLLENOSIS-INDUCING POLYPEPTIDE, PROCESS FOR PREPARING THE SAME, AND USES THEREOF

BACKGROUND OF THE INVENTION

1. Field of the Invention

The present invention relates to a novel polypeptide which induces pollenosis and to a process to produce the same, as well as to a desensitization agent for treating, preventing and/or diagnosing pollenosis.

2. Description of the Prior Art

For ten and several years, the number of patients, who complain about rhinitis and conjunctivitis due to pollenosis, has been increasing in Japan in early spring. Pollenosis frequently receives much publicity from the press because the number is significantly increasing and because it occurs in early spring at which a variety of events, festivals and the like are successively held. Therefore, pollenosis has become one of the problems of the public health which could not be ignored.

It is said that pollenosis is a sort of allergies which is mainly induced by an allergen present in cedar pollens (the wording "cedar" as referred to in the invention means *Cryptomeria japonica* and plants of the genus Cedrus), i.e., a cedar pollen allergen. The invasion of such an allergen, dispersed in the air, into the body resulted in the formation of immunoglobulin E antibody specific to the allergen. When the body being in such conditions is re-invaded by a cedar pollen, both a cedar pollen allergen present in the invaded pollen and the already formed immunoglobulin E antibody induce an immunoreaction to cause an allergic symptom.

Until now, it is known that at least 2 different types of allergens with different antigenicities are contained in cedar pollens. The one is an allergen, which is now called "*Cry j* I", as reported by Yasueda at al. in *Journal of Allergy and Clinical Immunology*, Vol.71, No.1, Part 1, pp.77–86 (1983), and the other is an allergen, which is now called "*Cry j* II", as reported by Taniai et al. in *FEBS LETTERS*, Vol.239, No.2, pp.329–332 (1988) or reported by M. SAKAGUCHI et al. in *Allergy*, No.45, pp.309–312 (1990). Usually, cedar pollens contain *Cry j* I and *Cry j* II in a weight ratio of about 50:1 to 5:1, and most of the sera collected from patients with pollinosis react with both *Cry j* I and *Cry j* II. Sawatani et al. reported in *Japanese Journal of Allergology*, Vol.42, No.6, pp.738–747 (1993) that *Cry j* II exerts the same level of antigenicity as that exerted by *Cry j* I when assayed on intradermal test (IT) and radioallergosorbent test (RAST).

As described above, several cedar pollen allergens have been isolated and revealed for their properties and characteristics to some extent, and because of this there appears some possibilities to treat and/or prevent pollenosis by administering a purified preparation of a cedar pollen allergen to a human for desensitization. Recently, desensitization agents for such a purpose have proposed: For example, Japanese Patent Laid-Open Nos.156,926/89 and 93,730/91 propose a method to administer to human a conjugate as desensitization agent prepared by covalently binding pullulan as a polysaccharide with an allergen having a partial amino acid sequence of Asp-Asn-Pro-Ile-Asp-Ser-or Ala-Ile-Asn-Ile-Phe-Asn- at the N-terminal. Since pollenosis-inducing allergens are not restricted to *Cry j* I and *Cry j* II, other pollenosis-related allergens should be urgently isolated and their properties and characteristics revealed to establish an accurate diagnosis and an effective desensitization therapy of pollenosis.

SUMMARY OF THE INVENTION

In view of the foregoing, the present invention was made and one object of the present invention is to provide a novel polypeptide which induces pollenosis.

It is a further object of the present invention to provide a method to prepare the polypeptide.

It is yet another object of the present invention to provide the use of the polypeptide as desensitization agent.

DETAILED DESCRIPTION OF THE INVENTION

The present invention relates to a novel polypeptide which induces pollenosis and to a process to produce the same, as well as to a desensitization agent for treating, preventing and/or diagnosing pollenosis.

The first object of the present invention is overcome by a polypeptide having the following physicochemical properties (hereinafter designated as "polypeptide"):

(1) Molecular weight
  40,000±5,000 daltons on sodium dodecyl polyacrylamide gel electrophoresis (SDS-PAGE);

(2) Isoelectric point (pI)
  9.5±0.5 on isoelectrophoresis;

(3) Partial amino acid sequence containing the N-terminal
  Possessing a partial amino acid sequence containing the N-terminal as shown by X-Arg-His-Asp-Ala-Ile-, where the symbol "X" means an amino acid or an oligopeptide selected from the group consisting of Ser- (residues 6–11 of SEQ ID NO:1); and Arg-Lys-Val-Glu-His-Ser- (SEQ ID NO:1)

(4) Ultraviolet absorption spectrum
  Exhibiting the maximum absorption spectrum at a wave length of around 280 nm;

(5) Solubility in solvent in solvent
  Soluble in water, physiological saline and phosphate buffer;

(6) Biological activity
  Inducing pollenosis.
  Binding to immunoglobulin E antibody collected from blood of a patient with pollenosis; and (7) Stability
  Being inactivated in an aqueous solution (pH 7.2) when incubated at 100° C. for 10 minutes.
  Substantially not inactivated in an aqueous solution (pH 7.2) even when allowed to stand at 4° C. for one month.

The second object of the present invention is overcome by extracting cedar pollens with an aqueous solvent, and recovering the polypeptide from the resultant extract.

The third object of the present invention is overcome by a desensitization agent which contains the polypeptide as effective ingredient.

As described hereinafter, the polypeptide is a novel substance having specific properties which are entirely different from those of conventional allergens of cedar pollens.

The present process facilitates the production of the polypeptide from cedar pollens in an increased yield.

The desensitization agent according to the present invention exerts a considerably-high desensitization activity when administered to mammals including humans.

The present invention relates to a novel polypeptide which induces pollenosis. During the research of cedar pollen allergens, we found there exists an unknown allergen in cedar pollens. We isolated such allergen by employing a combined use of column chromatography as main technique and other purification methods, and investigated the properties and characteristics to reveal that the reality is a polypeptide having different properties and characteristics from those of conventional allergens of cedar pollens.

The following experiments explain the specific properties and characteristics of the polypeptide according to the present invention:

EXPERIMENT 1

Purification of polypeptide

One part by weight of a cedar pollen collected from a male flower of "ura-sugi" or *Cryptomeria japonica*, grown in Akita, Japan, was suspended in and extracted with about 16 parts by weight of an aqueous solution of 0.125M sodium hydrogen carbonate (pH 8.2) while stirring at 4° C. for one hour, followed by centrifuging the resultant extract to obtain a supernatant. The sediment was treated similarly as above to obtain a supernatant which was then pooled with the above supernatant. To the solution was added 0.1 w/v % "CETAVLON", hexadecyltrimethylammonium bromide, commercialized by Sigma, Chemicals Co., St. Louis, USA, and the mixture was centrifuged to obtain a supernatant which was then mixed with ammonium sulfate to give a saturation degree of 80 w/v % to salt out proteinaceous components. The resultant sediment was dialyzed against 50 mM Tris-HCl buffer (pH 7.8) for 10 hours, filtered and fed to a column packed with DEAE-SEPHADEX® which had been previously equilibrated with 50 mM Tris-HCl buffer (pH 7.8), followed by recovering non-adsorbed fractions by feeding 50 mM Tris-HCl buffer (pH 7.8) to the column. The non-adsorbed fractions were pooled, adjusted to pH 5.0 by the addition of acetic acid, and fed to a column packed with of CM-SEPHADEX® which had been previously equilibrated with 10 mM acetate buffer (pH 5.0). The column was washed by feeding thereto 10 mM acetate buffer (pH 5.0), and fed with an eluant of 0.3M sodium chloride and 0.1M phosphate buffer (pH 7.0) to elute proteinaceous components. The fractions containing the proteinaceous components were pooled and fed to a column packed with "MONO-S" which had been previously equilibrated with 10 mM phosphate buffer (pH 5.0), and the column was fed with a linear gradient buffer of sodium chloride increasing from 0M to 0.5M in 10 mM Tris-HCl buffer (pH 7.0) to obtain the objective polypeptide in fractions with a concentration of 0.4M sodium chloride. The fractions were pooled, concentrated in usual manner and lyophilized for the use of the following experiments. The yield of the polypeptide was about 0.006 w/w % against the material cedar pollen, on a dry solid basis (d.s.b.).

EXPERIMENT 2

Physicochemical properties of polypeptide

In this experiment the purified polypeptide obtained in Experiment 1 was studied to determine its physicochemical properties.

EXPERIMENT 2-1

Molecular weight

In accordance with the method as reported by U. K. Lemuli in *Nature*, Vol.227, pp.680–685 (1970), the purified polypeptide was assayed on SDS-PAGE to show a major band in a position corresponding to 40,000±5,000 daltons. The molecular markers used in this experiment were calf serum albumin with a molecular weight of 67,000 daltons, ovalbumin with a molecular weight of 45,000, carbonic anhydrolase with a molecular weight of 30,000 daltons, chymotrypsinogen A with a molecular weight of 25,000 daltons, and cytochrome C with a molecular weight of 12,000 daltons.

A fraction corresponding to 40,000±5,000 daltons was transferred from the gel to a nitrocellulose membrane, and treated with an antibody of anti-cedar pollen allergen derived from mice and an anti-mouse immunoglobulin antibody, derived from goats, labelled with peroxidase from horseradish, to exhibit a distinct immunostaining. This indicates that the polypeptide is one of the cedar pollen allergens.

EXPERIMENT 2-2

Isoelectric point

The isoelectric point of the purified polypeptide was 9.5±0.5 when assayed on isoelectrophoresis.

EXPERIMENT 2-3

Partial amino acid sequence containing the N-terminal

Partial amino acid sequences containing the N-terminal of the purified polypeptide were analyzed on "MODEL 473 A", an amino acid sequencer commercialized by Applied Biosystems, Inc., Foster City, USA to reveal the following 2 partial amino acid sequences of:

(1) Ser-Arg-His-Asp-Ala-Ile- (residues 6–11 of SEQ ID NO:1) and (2) Arg-Lys-Val-Glu-His-Ser-Arg-His-Asp-Ala-Ile- (SEQ ID NO:1)

EXPERIMENT 2-4

Partial amino acid sequence containing the C-terminal

Four hundred µg of the purified polypeptide in Experiment 1 was placed in a reaction tube, and dissolved in 300 µl of 6M guanidine hydrochloride and 10 mM EDTA in 0.5M Tris-HCl buffer (pH 8.5). The tube was filled with nitrogen gas and mixed with adequate amounts of 4-vinylpyridine and tri-n-butylphosphine. The polypeptide in the resultant mixture was allowed to stand in a light-shielded place overnight to effect pyridylethylation. The reaction mixture thus obtained was dialyzed against distilled water, and the dialyzed solution was recovered, lyophilized, dissolved in 300 µl of 0.05M N-ethylmorphine acetate buffer (pH 8.7), mixed with 5 µg lysylendopeptidase, and incubated at 37° C. for 16 hours. Thereafter, the resultant mixture was heated at about 100° C. for 5 min to suspend the enzymatic reaction, and fed to a column packed with anhydrotrypsine agarose which had been previously equilibrated with 0.05M acetate buffer (pH 5.0) containing 0.02M calcium chloride, followed by recovering non-adsorbed fractions.

Among the non-adsorbed fractions, the objective fractions containing the polypeptide components were collected, concentrated, fed to "218TP54", a column for reverse-phase high-performance liquid chromatography, commercialized by Vydac, California, USA, which had been previously equilibrated with 0.1 v/v % aqueous trifluoroacetate solution, and eluted with water-soluble acetonitrile containing 0.1 v/v % trifluoroacetate at a flow rate of 0.5 ml/min while the concentration of acetonitrile was increasing at a rate of one v/v % per minute and the eluate was monitoring at a wave length of 214 nm. From the resultant eluate containing the polypeptide components were recovered, concentrated and analyzed their amino acid sequences on "MODEL 473A", an amino acid sequencer commercialized by Applied Biosystems, Inc., Foster City, USA, to reveal that the polypeptide has a partial amino acid sequence containing the C-terminal as shown by -Asn-Leu-Ser-Pro-Ser (SEQ ID NO:2).

EXPERIMENT 2-5

Ultraviolet absorption spectrum

By using a spectrophotometer the ultraviolet absorption spectrum of the purified polypeptide in Experiment 1 was measured in an aqueous solution to show the maximum absorption spectrum at a wave length of around 280 nm.

EXPERIMENT 2-6

Solubility in solvent

The solubility of the purified polypeptide in Experiment 1 was tested in usual manner to reveal that it was soluble in water, physiological saline and phosphate buffer.

EXPERIMENT 2-7

Biological activity

The polypeptide according to the present invention has properties of binding to an immunoglobulin E antibody obtained from blood of patients with pollenosis, and induces the growth of T-cells which specifically react with the polypeptide.

EXPERIMENT 2-7(a)

Test on binding to immunoglobulin E antibody

To 96-well microplate was adsorbed the purified polypeptide in Experiment 1 in an amount of one µg/well, and a serum preparation prepared from a healthy volunteer or a patient with pollenosis was added to the wells in an amount of 100 µl/well, followed by incubating the microplate at 37° C. for 2 hours. The microplate was washed with 0.1M phosphate buffer (pH 7.2) containing 0.1 v/v % calf serum albumin to remove non-adsorbed serum, and an anti-human immunoglobulin E antibody, derived from goat, labelled with peroxidase from horseradish, was added to the wells of the microplate in an amount of 100 µl/well, followed by further incubating the microplate at 37° C. for 2 hours. Thereafter, the microplate was washed with a fresh preparation of the same phosphate buffer as used above to remove non-adsorbed antibody, and to each well of which was added 100 µl of 0.1M citrate buffer (pH 5.0) containing 0.5 mg/l of o-phenylenediamine and 0.03 v/v % hydrogen peroxidase to effect coloration, followed by measuring the absorbance of a solution in each well at 492 nm.

As a result, the absorbance in the system using the serum of a healthy volunteer was about 0.1, while that in the system using the serum of a patient with pollenosis was as high as about 2.0, and this indicates that the present polypeptide specifically binds to immunoglobulin E antibodies contained in the blood of patients with pollenosis. Furthermore, these results confirm the fact that the present polypeptide is a substance causative of pollenosis, i.e., it has a property to induce pollenosis.

EXPERIMENT 2-7(b)

Test on T-cell growth induction

By using ficoll-hypaque gradient centrifugation, mononuclear cells were isolated from peripheral blood which had been collected from patients with pollenosis and supplemented with heparin. The mononuclear cells were suspended in RPMI 1640 medium (pH 7.0) supplemented with 10 v/v % AB serum to give a cell density of $1 \times 10^6$ cells/ml, admixed with 20 µg/ml of the purified polypeptide in Experiment 1, and intubated in an incubator at 37° C. for 5 days in 5 v/v % $CO_2$ atmospheric conditions. Thereafter, 50 units/ml of a recombinant human interleukin 2 was added to the resultant culture which was then further incubated similarly as above for 9 days. The resultant cells pretreated in this manner were used in the following T-cell growth test.

To 96-well microplate were added $4 \times 10^4$ cells/well of the mononuclear cells suspended in RPMI 1640 medium (pH 7.0) supplemented with 10 v/v % AB serum, $1 \times 10^6$ cells/well of peripheral mononuclear cells which had been collected from the same patient with pollenosis and incubated at 37° C. for 30 min in the presence of 50 µg/ml mitomycin C, 50 µg/ml of the purified polypeptide in Experiment 1, and a fresh preparation of the same medium as used above to give a total volume of 200 µl/well. The cells were successively incubated under 5 v/v % $CO_2$ atmospheric conditions at 37° C. for 2 days, admixed with 0.5 µCi/well $^3$H-thymidine, and incubated for one day, followed by counting the uptake amount of $^3$H-thymidine on a scintillation counter. In parallel, a system using a medium free of the present polypeptide was arranged as control and similarly treated as above.

As a result, the control system showed about 300 cpm of $^3$H-thymidine uptake, while the system with the polypeptide showed about 6,500 cpm of $^3$H-thymidine uptake per 50 µg/ml of the purified polypeptide, and this revealed that the purified polypeptide might strongly accelerate the T-cell growth in blood of pollenosis patients. This also means that the polypeptide has an antigenicity.

EXPERIMENT 2-8

Stability

No residual activity was observed when the purified polypeptide in Experiment 1 was incubated in an aqueous solution (pH 7.2) at 100° C. for 10 min. No substantial loss of activity was observed after a 1-month incubation of the purified polypeptide in an aqueous solution (pH 7.2) at 4° C.

Any polypeptide having these properties has not yet been known, and this concludes that it is a novel substance.

Now explaining the process to produce the present polypeptide, it can be prepared by collecting pollens from cedar such as "omote-sugi" or "ura-sugi", i.e. *Cryptomeria japonica*, extracting the pollen with an aqueous solvent, and purifying the extract. The methods used to extract the present polypeptide from cedar pollens in the invention are generally those which comprise collecting pollen from male flowers of cedar; suspending the pollen in water or an aqueous solvent such as those of a readily water-soluble organic solvent of methyl alcohol, ethyl alcohol, acetone or the like, or in an aqueous solvent admixed with an adequate amount of a stabilizer or the like; and soaking the pollen while stirring if needs arise in such a solvent at a temperature lower than 10° C., preferably, about 0°–5° C., for 30 min or longer, preferably, about 1–2 hours. Depending on the conditions of a cedar pollen used, the aforesaid procedure is usually carried out 1 to 5 times to extract most of the polypeptide from the material cedar pollen.

The polypeptide in the resultant extract can be purified by conventional techniques in general used in this field. Partially-purified polypeptides can be obtained from the extract by using a method such as a salting out, dialysis, filtration, centrifugation, gel filtration chromatography, etc. Such a partially-purified polypeptide generally contains cedar pollen allergens such as *Cry j* I together with the present polypeptide. In case a more highly-purified polypeptide is required, it can be obtained by removing components such as Cry j I and contaminants other than the present polypeptide with one or more methods such as gel filtration chromatography, ion-exchange chromatography, affinity chromatography, gel electrophoresis, isoelectrophoresis, etc.

The partially purified- and highly purified-polypeptides thus obtained can be arbitrarily incorporated into or used as desensitization agent for diagnosing, treating and/or preventing pollenosis. The purified polypeptide is useful as antigen for detecting immunoglobulin E antibodies, which have a specificity to the polypeptide, for qualitative and quantitative analyses on enzyme immunoassay and radio-immuno assay, and extensively applicable in the diagnosis of pollenosis and the scientific study to reveal the induction mechanisms of allergies in general.

The following examples concretely explain the process to produce the present polypeptide:

EXAMPLE A-1

Preparation of partially-purified polypeptide

One part by weight of a cedar pollen prepared from a male flower of "ura-sugi", i.e. Cryptomeria japonica, grown in Akita, Japan, was suspended in about 16 parts by weight of an aqueous solution of 0.125M sodium hydrogen carbonate (pH 8.2) to effect extraction while stirring at 4° C. for one hour, followed by centrifuging the resultant extract to obtain a supernatant. The sediment was treated similarly as above to obtain a supernatant which was then pooled with the above supernatant. To the mixture was added 0.1 w/v % "CETAVLON", hexadecyltrimethylammonium bromide commercialized by Sigma, Chemicals Co., Louis, USA, and the mixture was centrifuged to obtain a supernatant which was then mixed with ammonium sulfate to give a saturation degree of 80 w/w % to salt out proteinaceous components. The resultant sediment was dialyzed against 50 mM Tris-HCl buffer (pH 7.8) for 10 hours, and the dialyzed resultant was filtered to obtain a filtrate which was then fed to a column packed with DEAE-SEPHADEX® which had been previously equilibrated with 50 mM Tris-HCl buffer (pH 7.8), followed by recovering non-adsorbed fractions. The non-adsorbed fractions were pooled, adjusted to pH 5.0 by the addition of acetic acid, and fed to a column packed with "CM-SEPHADEX" which had been previously equilibrated with 10 mM acetate buffer (pH 5.0). The column was washed by feeding thereto 10 mM acetate buffer (pH 5.0), and fed with an eluant consisting of 0.1M phosphate buffer (pH 7.0) and 0.3M sodium chloride to elute the proteinaceous components. Thereafter, the resultant eluate was concentrated and lyophilized to obtain a partially-purified polypeptide containing Cry j I along with the present polypeptide. The yield was about 0.1% against the weight of the material cedar pollen, d.s.b.

The partially purified polypeptide thus obtained can be suitably used as a desensitization agent for diagnosing, treating and/or preventing pollenosis.

EXAMPLE A-2

Purified polypeptide

A partially-purified polypeptide obtained by the method in Example A-1 was dissolved in a small amount of distilled water, and the solution was fed to a column packed with "MONO-S" which had been previously equilibrated with 10 mM phosphate buffer (pH 5.0). The column was fed with a linear gradient buffer of salt increasing from 0M to 0.5M in 10 mM Tris-HCl buffer (pH 7.0), followed by the elution of the present polypeptide at a salt concentration of 0.4M. Thereafter, the eluate was concentrated and lyophilized to obtain a purified polypeptide substantially comprising the present polypeptide. The yield was about 0.006% against the weight of the material cedar pollen, d.s.b.

The purified polypeptide can be suitably used as desensitization agent for diagnosing, treating and/or preventing pollenosis, as well as being used as antigen for enzyme immunoassay or radioimmunoassay.

The uses of the present polypeptide will be explained with reference to the following examples and experiments.

Since the present polypeptide is one of the major substances causative of pollenosis, it can be extensively used in a variety of medicaments such as a desensitization agent for diagnosing, treating and/or preventing pollenosis. The desensitization agent according to the present invention comprises as an effective ingredient the present polypeptide or the later described conjugate of the polypeptide and a specific saccharide. As regards a desensitization agent directed to diagnosis of pollenosis, it can be generally prepared by mixing with a carrier a partially purified- or highly purified-polypeptide prepared by the aforesaid methods. As regards a desensitization agent directed to the treatment and/or prevention of pollenosis, it can be prepared into a conjugate prior to the mixing as mentioned above by covalently binding the present polypeptide with a specific saccharide.

The specific saccharides referred to in the inventions include those which can covalently bind with the present polypeptide into conjugates whereby the desensitization efficacy of the polypeptide is significantly augmented and/or the side effects are satisfactorily reduced. Examples of such a saccharide are homo or heteropolysaccharides such as starch, amylose, dextran, polysucrose, pullulan, elsinan, curdlan, gum arabic, gum tragacanth, guar gum, xanthan gum, carrageenan, cellulose, glucomannan, chitosan, lipopolysaccharides, and their derivatives and partial hydrolysates. Usually, the average molecular weight of such a saccharide is in the range of about 500–10,000,000 daltons, preferably, about 10,000–1,000,000 daltons. Among these saccharides, pullulan and elsinan, which consist essentially of repeating maltotriose units, as well as their partial hydrolysates are prepared with the polypeptide into conjugates having an activity of inducing immunoglobulin G and M antibodies which are effective for desensitization by a large margin when administered to mammals including human, but do not substantially form immunoglobulin E antibody which is a major factor causative of unsatisfactory side effects including anaphylactic shock. These properties are advantageously useful in the desensitization therapy which requires a repeated administration of medicaments in order to attain a considerably-high effect without a fear of causing unsatisfactory side effects.

For example, lipopolysaccharides derived from microorganisms of Escherichia coli, Salmonella, Serratia, etc. and their partial hydrolysates exert the following features when prepared into conjugates with the present polypeptide: Such a lipopolysaccharide increases the affinity of the polypeptide against the mucosae of mammals and significantly improves the intake efficiency of the polypeptide. For this reason, conjugates of the present polypeptide and the saccharides are advantageously useful as desensitization agents which are premised on percutaneous or permucosal administration.

Usually, such a conjugate can be prepared by reacting the present polypeptide with an activated saccharide or by bridging the polypeptide with a saccharide by using a reagent having one or more active functional groups. Examples of such a reaction are the diazo method, peptide method, alkylation method, bridging method, amide binding method, peroxidase oxidation method, disulfide binding method, etc., and these methods per se are known in this art. A representative of such a method is described in detail, for example, in Japanese Patent Laid-Open No.93,730/91. The ratio of the polypeptide against a saccharide at the initiation of the reaction suitably used in the invention is usually in the range of about 1:0.001 to 1:1,000, preferably, about 1:0.01 to 1:100, d.s.b. Depending on the reaction methods used, molecules of the polypeptide readily bind each other when the ratio is below the above range, while molecules of the saccharide readily react with each other when the ratio exceeds the range. Anyway, any ratios other than those specified in the invention result in reductions of reactivity and purification efficiency of the reaction products, and this leads me to conclude that the above-specified ratios are the best mode. The reaction temperature, pH and time used in the present invention are chosen so as not to inactivate or decompose the polypeptide or to reduce the side reactions as much as possible, and, usually, a temperature of about 0°–100° C. and a pH of about 0.1–12 are suitably used to complete the reaction within about 0.1–50 hours.

The conjugates obtained by the above reaction can be purified by conventional methods in general such as dialysis, salting out, filtration, concentration, centrifugation, gel filtration chromatography, ion-exchange chromatography, affinity chromatography, gel electrophoresis, isoelectrophoresis, etc., and, if necessary, such a conjugate can be purified by an appropriate combination use of the above methods. The resultant purified conjugates may be concentrated and lyophilized into liquid or solid products to meet to final use.

The desensitization agent according to the present invention includes the aforesaid polypeptide and/or conjugates, and other compositions comprising either of the polypeptide or conjugates along with a physiologically acceptable carrier, excipient, diluent, adjuvant and/or stabilizer, and other one or more medicaments, for example, an antihistaminic and an anti-inflammatory agent such as steroid hormone or disodium cromoglycate. The desensitization agent may be in a dose form, i.e. those which contain the present polypeptide or conjugates in an amount suitable for a dose per day or in an amount up to 4 times by integers or up to 1/40 times of the dose, and may be a physically separated form suitable for a prescribed administration. Examples of the form of such a pharmaceutical agent are a powder, parvule, granule, pearl, tablet, capsule, troche, syrup, emulsion, ointment, emplastrum, pap, suppository, collyrium, nebula, spray, injection, etc.

Now explaining the use of the present desensitization agent, it can be used similarly as conventional desensitization agents in general containing allergens of cedar pollens. In case of using the present desensitization agent for diagnosing pollenosis, patients are scratched on their skin surfaces with a care not to bleed by using conventional tests known as the scratch or intradermal-test, and an adequate amount of the present desensitization agent for diagnosis was dropped on the scratched sites, or they are intradermally injected with an adequate amount of the desensitization agent. Thereafter, the occurrence and the size of urtica formed 15–30 min after the dropping or injecting are checked and measured, and it was determined to be positive when the size exceeded a prescribed level.

In the treatment using the present desensitization agent, an appropriate dose and application thereof are usually determined based on the results of the aforesaid diagnosis. Patients with a positive result in the diagnosis are orally or parenterally administered with the present desensitization agent containing a conjugate of the present polypeptide and a specific saccharide. Depending on the symptoms and/or administration routes, patients are usually administered repeatedly via the route of an intradermal, subcutaneous, intramuscular, intraperitoneal or permucosal administration with the present desensitization agent at a dose of about 0.0001–100,000 ng/shot/adult, preferably, a dose of about 0.001–10,000 ng/shot/adult and a frequency of one shot per week or month for about 1–12 months while usually increasing the dose. In case of using the present desensitization agent in the prevention of pollenosis, approximately the same dose and application as used in the treatment of pollenosis can be used, and patients are usually administered repeatedly with the desensitization agent at a dose of about 0.0001–100,000 ng/shot/adult, preferably, a dose of abut 0.001–10,000 ng/shot/adult, and a frequency of one shot per week or month for about 1–6 months while usually increasing the dose via the route of an intradermal, subcutaneous, intramuscular or permucosal administration while observing the patients' conditions and symptoms. When the present desensitization agent is repeatedly administered to patients in a prescribed time interval from the beginning of autumn to the following early spring, the expected allergic symptoms of the patients, which might be induced in the forthcoming season, would be substantially reduced or completely avoided.

The desensitization agent according to the present invention will be described concretely with reference to the following several examples:

EXAMPLE B-1

Dried injection

Two g of a purified pullulan having an average molecular weight of about 200,000 daltons was dissolved in 100 ml distilled water, and the solution was mixed with 2ml of 1.7 w/v % cyanuric chloride in acetone solution. Thereafter, the resultant mixture was reacted by allowing it to stand at 4° C. or lower for 2 hours in an ice-chilled bath while the pH was controlled to around 7 by the addition of 5 w/v % aqueous sodium carbonate solution. The resultant solution containing an activated pullulan was mixed with 40 mg of a purified polypeptide obtained by the method in Example A-2, and allowed to react at 37° C. for 5 hours under stirring conditions. After completion of the reaction the resultant was mixed with one w/v % glycine and incubated at 37° C. for one hour while stirring to block the intact activated groups, and the resultant mixture was dialyzed against 0.01M acetate buffer (pH 5.0) for 5 hours, fed to a column packed with "CM-SEPHADEX" which had been previously equilibrated with 0.01M acetate buffer (pH 5.0), followed by recovering the present conjugate of the polypeptide and pullulan from non-adsorbed fractions. The conjugate was in usual manner dissolved in physiological saline supplemented with human serum albumin as stabilizer to give a final concentration of about 100 ng/ml, and the solution was membrane filtered, distributed into sterile vials by 2 ml aliquots, lyophilized and cap sealed.

In use, one ml distilled water for injection is added to each vial, and the contents are dissolved to homogeneity prior to administration. The product, which contains the conjugate of the polypeptide and pullulan as effective ingredient, can be arbitrarily useful as dried injection for treating and/or preventing pollenosis.

EXAMPLE B-2

Injection

One g of CM-cellulose having an average molecular weight of about 20,000 daltons was dissolved in 200 ml distilled water, and the solution was mixed with 2 g 1-ethyl-3-(3-dimethylaminopropyl)carbodiimide-methiozide, followed by reacting the resultant solution at ambient temperature for 2 hours while stirring and keeping the pH at around 4 by the addition of 1N hydrochloride. The reaction mixture was dialyzed against distilled water for 24 hours, and the dialyzed solution was recovered, mixed with 30 mg of a purified polypeptide obtained by the method in Example A-2, and allowed to stand to react the contents at ambient temperature and pH 4.5 for 15 hours. Thereafter, the resultant conjugate in the reaction mixture was purified similarly as in Example B-1, concentrated, dissolved in 50 v/v % aqueous glycerine solution, membrane filtered, distributed into sterile vials by 2 ml aliquots, and cap sealed.

With reference to the diagnostic results in the scratch- or intradermal-test, the product is admixed with 100-fold to 100,000-fold volumes of 50 v/v % aqueous glycerine solution to dilute the contents to homogeneity prior to administration. The product containing a conjugate of the present polypeptide and CM-cellulose can be arbitrarily used as desensitization agent for treating and/or preventing pollenosis.

EXAMPLE B-3

Liquid preparation

One hundred mg of a purified lipopolysaccharide derived from a microorganism of the genus Salmonella in 25 ml of an about 4° C. aqueous solution of sodium acetate with a saturation degree of 50 w/v %, and the resultant solution was adjusted to pH 9.0 by the addition of 0.5 N sodium hydroxide, followed by adding thereto drop by drop one ml anhydrous dioxane containing 20 μl bromoacetyl bromide while keeping the pH at around 8.5. Thereafter, the resultant solution was adjusted to a pH of about 4.5 by the addition of 6N acetic acid, dialyzed against 4° C. distilled water for 48 hours to obtain an aqueous solution containing an activated lipopolysaccharide. To the aqueous solution was added 40 mg of a purified polypeptide obtained by the method in Example A-1, followed by allowing the mixture to react at ambient temperature for 48 hours while keeping the pH at about 4.5. Thereafter, the reaction mixture was purified similarly as in Example B-1, concentrated, lyophilized to obtain a solid conjugate of the present polypeptide and lipopolysaccharide. The solid conjugate was dissolved in distilled water containing one w/v % purified gelatin as stabilizer to give a final concentration of 100 ng/ml, and the resultant solution was in usual manner membrane filtered to obtain a liquid preparation.

The product, containing a conjugate of the present polypeptide and lipopolysaccharide, can be arbitrarily used as liquid preparation for a collunarium, nebula or oral spray for treating and/or preventing pollenosis.

EXAMPLE B-4

Sublingual tablet

Two g of a purified elsinan having an average molecular weight of about 200,000 daltons was dissolved to homogeneity in 400 ml distilled water, and the solution was adjusted to pH 10.7 by the addition of 1N sodium hydroxide, gradually admixed with 3 g cyanogen bromide, and reacted for one hour. The reaction mixture was adjusted to pH 5.0 by the addition of 1N hydrochloride, and dialyzed against cold water for 10 hours while keeping at the pH, followed by recovering an aqueous solution containing an activated elsinan. To the aqueous solution was added 20 mg of a purified polypeptide obtained by the method in Example A-2, and the resultant was allowed to stand at ambient temperature for 24 hours to react the contents. After completion of the reaction, the reaction mixture was mixed with 3-fold volumes of acetone, followed by recovering the formed precipitate, dissolving it in 0.01M acetate buffer (pH 5.0), and removing insoluble substances by centrifugation. The supernatant thus obtained was fed to a column packed with "CM-SEPHADEX" which had been previously equilibrated with 0.01M acetate buffer (pH 5.0), followed by recovering fractions containing a conjugate of the present polypeptide and elsinan. The fractions were in usual manner pooled, membrane filtered, concentrated, pulverized and mixed to homogeneity with "FINETOSE®", an anhydrous crystalline α-maltose powder commercialized by Hayashibara Co., Ltd., Okayama, Japan. The resultant mixture was in usual manner tabletted with a tabletting machine to obtain tablets, 200 mg weight each, containing 100 ng of the present polypeptide per tablet.

The product, having a satisfactory stability and applicability, can be arbitrarily used as sublingual agent for treating and/or preventing pollenosis.

EXAMPLE B-5

Diagnostic agent

Ten mg of a partially-purified polypeptide obtained by the method in Example A-1 was dissolved in 20 ml of physiological saline, and the solution was in usual manner membrane filtered, distributed in sterile vials by one ml aliquots, lyophilized and cap sealed.

The product is dissolved in one ml of distilled water for injection, and further diluted with 10 folds with a fresh preparation of the same distilled water prior to use in the diagnosis of pollenosis for the scratch- and intradermal-tests.

EXAMPLE B-6

Diagnostic agent

One mg of a purified polypeptide obtained by the method in Example A-2 was dissolved in 20 ml of 50 v/v % glycerine containing 5 w/v % sodium chloride, and the resultant solution was in usual manner membrane filtered and distributed into sterile vials by one ml aliquots.

The product is diluted by 20-fold with a 50 v/v % aqueous glycerine solution and used for the diagnosis of pollenosis by the scratch- and intradermal-tests.

The following several experiments explain the efficacy of the present desensitization agent:

EXPERIMENT 3

Animal experiment

This experiment was carried out to evidently show that the present conjugate of the present polypeptide and a specific saccharide exerts an efficacy on the treatment and/or prevention of pollenosis when actually administered to experimental animals.

EXPERIMENT 3-1

Prophylactic effect

Six female BALB/c mice, 10–12-week-old, in a group, were intraperitoneally injected with a desensitization agent obtained by the method in Example B-1 in a dose of one μg/mouse of the polypeptide per week over 3 weeks. One week after the final injection, the mice were induced pollenosis by injecting to them similarly as above 0.2 ml of a physiological saline, containing 4 mg aluminum hydroxide as adjuvant and one μg of a purified polypeptide obtained by the method in Example A-2 as antigen. The mice were sampled their blood immediately before and one week after the administration of the antigen, and the blood samples were examined for the amounts of immunoglobulin G and M antibodies specific to the polypeptide.

As a control system, mice were administered with a mixture containing a purified polypeptide, obtained by the method in Example A-2, and a purified pullulan having an average molecular weight of about 200,000 daltons in a weight ratio of 1:15, and treated similarly as above. The amount of immunoglobulin E antibody which is specific to the present polypeptide was assayed by the passive cutaneous anaphylaxis (PCA) reaction as reported by I. Mota and D. Wong in *Life Sciences*, Vol.8, No.16, Part II, pp.813–820 (1969), and the amount of immunoglobulin M antibody which is specific to the present polypeptide was assayed by the enzyme immunoassay as reported by S. YOSHITAKE et al. in *The Journal of Biochemistry*, Vol.92, No.5, pp.1, 413–1,424 (1982). The amount of each antibody was expressed with an average value of antibody titers of 6 mice. The results were as shown in Table 1.

human with the viewpoint of that immunoglobulin E antibody is known as major factor causative of unsatisfactory side effects including anaphylactic shock.

EXPERIMENT 3-2

Therapeutic effect by parenteral administration

Pollenosis was induced in 6 female BALB/c mice, 10–12-week-old, in a group, by intraperitoneally injecting them once a week over 3 weeks with 0.2 ml of a physiological saline containing one μg of a purified polypeptide as antigen, obtained by the method in Example A-2, and 4 mg aluminum hydroxide as adjuvant. One week after the final administration of the antigen, the mice were injected once a week over 3 weeks similarly as above with a desensitization agent obtained by the method in Example B-1 at a dose of 100 ng/mouse of the polypeptide, d.s.b. One week after the final administration of the desensitization agent, the mice were further administered only with the antigen to reinduce immunoglobulin E antibody. The blood of the mice was sampled immediately before the administration of the desensitization agent, one week after the final administration of

TABLE 1

| Desensitization agent | Immediately before administration | | One week after administration | | |
|---|---|---|---|---|---|
| | IgG + IgM | IgE | IgG + IgM | IgE | Judgement |
| Conjugate of polypeptide and pullulan | 250 | 0 | 950 | 4 | Present invention |
| Mixture of polypeptide and pullulan | 28 | 19 | 260 | 300 | Control |

Note:
In the Table, "polypeptide" means the present polypeptide; "IgG", immunoglobulin G; "IgM", immunoglobulin M; and "IgE", immunoglobulin E.

As is evident from the results in Table 1, compared with the control system, the system, wherein the mice had been previously administered with the desensitization agent containing the conjugate of the present polypeptide and pullulan, showed a relatively-high productivity of immunoglobulin G and M antibodies which are effective for desensitization, while the formation of immunoglobulin E antibody in the mice was substantially inhibited. The inhibitory activity of forming immunoglobulin E antibody, exerted by the present desensitization agent by administering it to mice, indicates that the agent can be safely and effectively used in the prevention of pollenosis of mammals including the desensitization agent, and one week after the reinduction of immunoglobulin E antibody, and the blood samples were assayed by the same method as in Experiment 3-1 for determining the amounts of immunoglobulin E, G and M antibodies which are specific to the polypeptide.

As a control system, mice were administered with a mixture, containing a purified polypeptide, obtained by the method in Example A-2, and a purified pullulan having an average molecular weight of about 200,000 daltons in a weight ratio of 1:15, in place of the desensitization agent as used above, and treated similarly as above. The results were as shown in Table 2.

TABLE 2

| Desensitization agent | Immediately before administration | | One week after administration | | One week after the reinduction of IgE | | |
|---|---|---|---|---|---|---|---|
| | IgG + IgM | IgE | IgG + IgM | IgE | IgG + IgM | IgE | Judgement |
| Conjugate of polypeptide and pullulan | 340 | 180 | 2,400 | 40 | 5,750 | 40 | Present invention |
| Mixture of polypeptide and pullulan | 350 | 180 | 460 | 350 | 2,650 | 1,340 | Control |

Note:
In the Table, "polypeptide" means the present polypeptide; "IgG", immunoglobulin G; "IgM", immunoglobulin M; and "IgE", immunoglobulin E.

As is evident from the results in Table 2, compared with the control system, the system, wherein the mice were administered with the present desensitization agent containing a conjugate of the present polypeptide and pullulan, resulted in the formation of relatively-large amounts of immunoglobulin G and M antibodies both after the administration of the desensitization agent and the reinduction of immunoglobulin E antibody. As regards immunoglobulin E antibody, the formation was substantially inhibited even before the administration of the desensitization agent and after the reinduction of immunoglobulin E antibody. These results confirm that pollenosis of mammals including human could be safely and effectively treated by the parenteral administration of the present desensitization agent containing the conjugate.

EXPERIMENT 3-3

Therapeutic effect by oral administration

Pollenosis was induced in 6 female BALB/c mice, 10–12-week-old, in a group, by intraperitoneally injecting them once a week over 3 weeks with 0.2 ml of a physiological saline containing one μg of a purified polypeptide as antigen, obtained by the method in Example A-2, and 4 mg aluminum hydroxide as adjuvant. One week after the final administration of the antigen, the mice were orally administered once a week over 3 weeks similarly as above with a sublingual agent, obtained by the method in Example B-4, at a dose of 100 ng/mouse of the polypeptide, d.s.b. One week after the final administration of the sublingual agent, the blood of the mice was, and the blood samples were assayed for the amounts of immunoglobulin A, G and E antibodies which are specific to the polypeptide.

As a control system, mice were orally administered with a solid mixture containing a purified polypeptide, obtained by the method in Example A-2, and a purified lipopolysaccharide derived from Salmonella in a weight ratio of 1:15, and treated similarly as above. The amounts of immunoglobulin A and G antibodies, which are specific to the present polypeptide, were assayed with the enzyme immunoassay (EIA) as reported by R. Maiolini et al. in *Journal of Immunological Methods*, Vol.6, pp.355–362 (1975), and the amount of immunoglobulin E antibody was assayed with the same method as in Experiment 3-1. The amounts of immunoglobulin A, G and E antibodies were respectively expressed with an average value of antibody titers of 6 mice. The results were as shown in Table 3.

tion of immunoglobulin E was substantially inhibited. These results confirm that the present desensitization agent containing the conjugate can safely and effectively treat pollenosis of mammals including human even when administered orally.

Although the data are not shown, significant therapeutic and/or prophylactic effects were exerted on pollenosis without a fear of causing unsatisfactory side effects even when mice, rats and guinea pigs were intradermally, subcutaneously, intramuscularly or intraperitoneally administered by conventional methods as used in this field with a desensitization agent obtained by the methods in Examples B-1 to B-4, or permucocutaneously administered with such a desensitization agent in the form of a collunarium, nebula or spray for oral cavity. It was revealed that such an effect was more augmented when there was used a conjugate of the present polypeptide and a saccharide, which consists essentially of repeating maltotriose units, such as pullulan or elsinan, and, in this case, the dose and administration period requisite for attaining the objective desensitization effect were less reduced or shortened as compared with conjugates prepared with other saccharides.

EXPERIMENT 3-4

Acute toxicity test

By using conventional method, mice, 20-day-old, were orally or intraperitoneally administered with therapeutic and/or prophylactic desensitization agents obtained by the method in Examples B-1 to B-4. As a result, it was revealed that the $LD_{50}$ of the desensitization agents was 1,000,000 ng/kg or more in any administration route. The results confirm that the present desensitization agent containing the present polypeptide and a specific saccharide can be used in pharmaceuticals for administering to mammals including human without a fear of causing side effects.

As is described above, the polypeptide according to the present invention is a novel substance causative of pollenosis. The polypeptide has a feature to induce pollenosis in mammals including human, and because of this it is widely applicable to desensitization agents for diagnosing, treating and/or preventing pollenosis, as well as to diagnosis of pollenosis using enzyme immunoassay and radioimmunoassay, and to researches for elucidating the mechanisms of allergy induction in general. More particularly, the conjugates of the polypeptide and a specific

TABLE 3

| Desensitization agent | Immediately before administration | | One week after administration | | |
|---|---|---|---|---|---|
| | IgA + IgG | IgE | IgA + IgG | IgE | Judgement |
| Conjugate of polypeptide and lipopolysaccharide | 310 | 150 | 2,100 | 30 | Present invention |
| Mixture of polypeptide and lipopolysaccharide | 320 | 170 | 430 | 300 | Control |

Note:
In the Table, "polypeptide" means the present polypeptide; "IgA", immunoglobulin A; "IgG", immunoglobulin G; and "IgE", immunoglobulin E.

As is evident from the results in Table 3, compared with the control system, the system, wherein the mice were administered with the desensitization agent containing the conjugate of the present polypeptide and the lipopolysaccharide, showed a relatively-large productivity of immunoglobulin A and G antibodies, while the producsaccharide according to the present invention are characteristic in that they induce the production of immunoglobulin antibodies which are effective for desensitization when administered to mammals including human, and do not substantially form immunoglobulin E antibody as major factor causative of unsatisfactory side effects such as anaphylactic shock. Because of these properties, the present desensitization agent effectively reduces the dose of an antigen and shortens the administration period requisite for the treatment and/or prevention of pollenosis. The polypeptide with these useful properties can be readily prepared from cedar pollens as material in a satisfactory-high yield by the present process.

The present invention exerts the aforesaid outstanding effects and has a great significance and contribution to the field.

While there has been described what is at present considered to be the preferred embodiments of the invention, it will be understood the various modifications may be made therein, and it is intended to cover in the appended claims all such modifications as fall within the true spirits and scope of the invention.

(5) Solubility:

Soluble in water, physiological saline and phosphate buffer;

(6) Biological activity

Inducing pollenosis by binding to immunoglobulin E antibody collected from blood of a patient with pollenosis; and (7) Stability Being inactivated in an aqueous solution (pH 7.2) when incubated at 100° C. for 10 minutes; Substantially not losing its activity in an aqueous solution (pH 7.2) when allowed to stand at 4° C. for one month.

2. The polypeptide in accordance with claim 1, which has a partial amino acid sequence containing the C-terminal as shown by -Asn-Leu-Ser-Pro-Ser as a C-terminal sequence (SEQ ID NO:2).

We claim:

1. A purified polypeptide having the following physico-chemical properties:
   (1) Molecular weight
      40,000±5,000 daltons on sodium dodecyl polyacrylamide gel electrophoresis (SDS-PAGE);
   (2) Isoelectric point (pI)
      9.5±0.5 on isoelectrophoresis;
   (3) Partial amino acid sequence containing the N-terminal as an N-terminal sequence Ser-Arg-His-Asp-Ala-Ile-, or Arg-Lys-Val-Glu-His-Ser-Arg-His-Asp-Ala-Ile- (SEQ ID NO: 1);
   (4) Ultraviolet absorption spectrum
      Exhibiting the maximum absorption spectrum at a wave length of around 280 nm;

3. The polypeptide in accordance with claim 1, which is derived from a cedar pollen.

4. A process for preparing the polypeptide of claim 1, which comprises extracting a cedar pollen with water or an aqueous solvent, and recovering the polypeptide from the resultant extract.

5. The process in accordance with claim 4, wherein the polypeptide is recovered from the resultant extract by using at least one method selected from the group consisting of salting out, dialysis, filtration, concentration, centrifugation, gel filtration chromatography, ion-exchange chromatography, affinity chromatography, gel electrophoresis and isoelectrophoresis.

6. The process in accordance with claim 4 wherein the polypeptide has a partial amino acid sequence containing the C-terminal as shown by -Asn-Leu-Ser-Pro-Ser as a C-terminal sequence (SEQ ID NO:2).

7. The process in accordance with claim 4, wherein said aqueous solvent is at least one member selected from the group consisting of aqueous solutions of methyl alcohol, ethyl alcohol and acetone.

8. A desensitization agent comprising a pharmaceutically-acceptable carrier and the polypeptide of claim 1 as an effective ingredient.

9. The desensitization agent in accordance with claim 8, wherein the polypeptide has a partial amino acid sequence containing the C-terminal as shown by -Asn-Leu-Ser-Pro-Ser as a C-terminal sequence (SEQ ID NO:2).

10. The desensitization agent in accordance with claim 8, which contains as a stabilizer at least one member selected from the group consisting of serum albumin and gelatin.

11. The desensitization agent in accordance with claim 8, wherein the polypeptide is obtainable by extracting a cedar pollen with water or an aqueous solvent, and purifying the resultant extract.

12. The desensitization agent in accordance with claim 11, wherein said aqueous solvent is at least one member selected from the group consisting of aqueous solutions of methyl alcohol, ethyl alcohol and acetone.

13. The desensitization agent in accordance with claim 8, wherein the polypeptide covalently binds to a saccharide.

14. The desensitization agent in accordance with claim 13, wherein the weight ratio of the polypeptide with respect to the saccharide is about 1:0.001 to 1:1,000, on a dry solid basis.

15. The desensitization agent in accordance with claim 13, wherein the covalent binding between the polypeptide and the saccharide is formed by reacting them at a pH of about 0.1–12 and a temperature of about 0°–100° C. for about 0.1–50 hours.

16. The desensitization agent in accordance with claim 13, wherein the saccharide is at least one member selected from the group consisting of starch, amylose, dextran, polysucrose, pullulan, elsinan, curdlan, gum arabic, gum tragacanth, guar gum, xanthan gum, carrageenan, cellulose, glucomannan, chitosan, lipopolysaccharides, and their derivatives and partial hydrolysates.

17. The desensitization agent in accordance with claim 16, wherein the saccharide has an average molecular weight in the range of about 500–10,000,000 daltons.

* * * * *

UNITED STATES PATENT AND TRADEMARK OFFICE
CERTIFICATE OF CORRECTION

PATENT NO. : 5,631,221
DATED : May 20, 1997
INVENTOR(S) : Kelzo Kohno et al.

It is certified that error appears in the above-indentified patent and that said Letters Patent is hereby corrected as shown below:

On title page, item [73], in the name of the Assignee, delete "Sibutsu" and insert therefor --Seibutsu--.

Signed and Sealed this

Second Day of December, 1997

Attest:

Attesting Officer

BRUCE LEHMAN

Commissioner of Patents and Trademarks